United States Patent [19]

Birtwistle et al.

[11] Patent Number: 5,078,991

[45] Date of Patent: * Jan. 7, 1992

[54] TOPICAL COMPOSITION

[75] Inventors: David H. Birtwistle; Peter Carter; David A. Rosser, all of Merseyside, England

[73] Assignee: Chesebrough-Pond's USA Co., Division of Conopco, Inc., Greenwich, Conn.

[*] Notice: The portion of the term of this patent subsequent to May 14, 2008 has been disclaimed.

[21] Appl. No.: 442,962

[22] Filed: Nov. 29, 1989

[30] Foreign Application Priority Data

Dec. 1, 1988 [GB] United Kingdom ............... 8828020

[51] Int. Cl.$^5$ .................. A61K 7/75; A61K 7/50
[52] U.S. Cl. ........................ 424/70; 252/109; 252/DIG. 13; 252/DIG. 5; 252/DIG. 14; 252/DIG. 16; 252/DIG. 17; 252/134.21; 252/174.22; 252/174.16; 514/772; 514/944; 514/975
[58] Field of Search ............ 514/772, 944, 975; 252/DIG. 14, DIG. 16, DIG. 17, DIG. 5, DIG. 13, 174.16, 174.21, 174.22, 109; 424/70

[56] References Cited

U.S. PATENT DOCUMENTS

| | | |
|---|---|---|
| 2,758,093 | 8/1956 | Ernst et al. ............. 252/DIG. 17 |
| 4,139,485 | 2/1979 | Imokawa et al. ............. 252/135 |
| 4,526,710 | 7/1985 | Fujisawa et al. ............. 252/545 |
| 4,758,376 | 7/1988 | Hirota et al. ............. 252/545 |

FOREIGN PATENT DOCUMENTS

| | | |
|---|---|---|
| 0077920 | 5/1983 | European Pat. Off. . |
| 0179277 | 4/1986 | European Pat. Off. . |
| 8901023 | 2/1989 | World Int. Prop. O. . |

*Primary Examiner*—Thurman K. Page
*Assistant Examiner*—Susan S. Rucker
*Attorney, Agent, or Firm*—Milton L. Honig

[57] ABSTRACT

An aqueous composition suitable for topical application to the skin or hair, comprises:

a. a dialkyl or dialkenyl phosphate salt (or mixtures thereof) having the structure (1):

$$R^{01}-(OCH_2CH_2)_a-O \diagdown_{\displaystyle P-OX}^{\displaystyle O} \atop R^{02}-(OCH_2CH_2)_b-O \diagup \quad (1)$$

where $R^{01}$ and $R^{02}$ are each chosen from branched or unbranched alkyl or alkenyl groups having an average of from 7 to 9 carbon atoms;

X is chosen from H, alkali metal, ammonium and substituted ammonium counterions;

a and b are each chosen from 0 or a value of from 1 to 4; and b. a cosmetically acceptable vehicle for the salt.

16 Claims, No Drawings

TOPICAL COMPOSITION

FIELD OF THE INVENTION

The invention relates to compositions suitable for topical application to the skin, (including the mucosae), and to the hair. In particular, the invention is concerned with highly improved detergent compositions suitable for cleansing the whole body surface, including the mouth.

BACKGROUND TO THE INVENTION AND PRIOR ART

The damaging effect of conventional detergents used to wash the body surface, particularly where young, tender or damaged skin is involved, has been the subject of intense study for many years in a search for milder-to-the-skin products, which not only cleanse the skin efficiently, but also leave the skin with a pleasant smooth silky feel after the skin surface has been dried off.

The use of certain mono- and di-alkyl phosphate salts for this purpose has been advocated in view of their mild characteristics, but some of this group of salts are used as antifoam agents because of their lather suppressant properties, and would therefore require careful formulation if lather control is not required.

To this end, U.S. Pat. No. 4,139,485 (Kao Soap Co. Ltd.) describes a detergent composition having low irritation properties on human skin, wherein the surfactant component is dialkyl or dialkenyl phosphate salt (DAP) and/or monoalkyl or monoalkenyl phosphate salt (MAP), each alkyl or alkenyl group having from 10 to 16 carbon atoms), the weight ratio of 'DAP' to 'MAP' being from 20:80 to 0:100. This system is stated to possess good detergency.

Also, in U.S. Pat. No. 4,526,710 Kao Corporation report a study to improve properties of detergent composition which make use of anionic phosphate surface active agents, which Kao maintain are highly innoxious and particularly mild to the skin. As a result, Kao have found that when phosphate ester salts having a specific ion pair, notably mono- or di-alkyl (C8-18) phosphates, are used in combination with alkanol amine salts of higher fatty acids and alkyl amine oxides, the detergency and foaming characteristics are remarkably improved.

Also, U.S. Pat. No. 4,758,376 (Kao) discloses an alternative composition, comprising an alkanolamine salt of a mono or dialkyl (C8-18) phosphate or mixtures thereof, to that described in U.S. Pat. No. 4,526,710 in which the problem of poor foaming due to the dialkyl phosphate salt is dealt with by incorporating with the phosphate a compound chosen from an amidoamine amphoteric surfactant or hydroxysulphobetaine, or an aliphatic lactylate or glycolate.

It is clear from a study of the three Kao references, that all the evidence on which their disclosures are based is restricted to alkyl phosphates or dialkyl phosphates in which the alkyl group has at least 10 carbon atoms. There is absolutely no reference at all to any evaluation of an alkyl phosphate ester or dialkyl phosphate ester salt where the alkyl group or groups contains only 9 carbon atoms, or less.

Applicants in their search for a mild surfactant for use in cleansing human skin or hair, with the added attribute that a full, soft lather is produced without necessarily incorporating a secondary surfactant such as those proposed by Kao, have unexpectedly discovered that a narrow range of certain dioctyl phosphate salts meet their requirements in this respect. Furthermore, closely related dialkyl phosphate salts immediately outside this narrow range surprisingly produce little or no lather of any note, under normal conditions of use. Evidence to substantiate this fact is given later in this specification. The compositions so obtained are accordingly capable of producing a superior lather volume and an outstanding lather creaminess. Also, the composition is so mild to the skin that it can safely be used for cleansing the mucosae, such as the mouth and the vagina, and other more delicate skin areas. It can also be used in shampoos for frequent, e.g. daily, hair washing, without risk of scalp irritation or damage attributable to harsher products. In addition to these excellent attributes, the ease of rinsing from hair or skin and superior silky-smooth after-use skin feel properties of the compositions, including freedom from skin roughness and erythema, have great consumer appeal.

DEFINITION OF THE INVENTION

Accordingly, the invention provides a composition suitable for topical application to the skin or hair, which comprises:

(a) from 1 to 99.9% by weight of a dialkyl or dialkenyl phosphate salt (or mixtures thereof) having the structure (1):

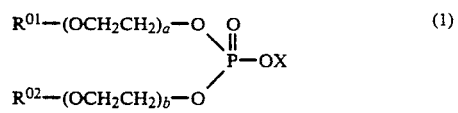

where $R^{01}$ and $R^{02}$ are each chosen from branched or unbranched alkyl or alkenyl groups having an average of from 7 to 9 carbon atoms;

X is chosen from H, alkali metal ammonium and substituted ammonium counterions;

a and b are each chosen from 0 or a value of from 1 to 4;

(b) from 0.01 to 99% by weight of a cosmetically acceptable vehicle for the salt.

DISCLOSURE OF THE INVENTION

The Dialkyl or Dialkenyl Phosphate Salt

The composition according to the invention comprises as a surfactant, a dialkyl or dialkenyl phosphate salt (or mixtures thereof) having the structure (1):

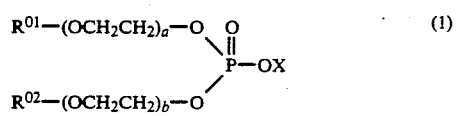

where $R^{01}$ and $R^{02}$ are each chosen from branched or unbranched alkyl or alkenyl groups having an average of from 7 to 9 carbon atoms;

X is chosen from H, alkali metal ammonium and substituted ammonium counterions;

a and b are each chosen from 0 or a value of from 1 to 4.

Examples of the dialkyl- and dialkenyl phosphate moiety include:
di-n-heptyl phosphate
di-n-octyl phosphate di-n-nonyl phosphate
di-(diethyleneglycol-mono-n-nonyl ether) phosphate
di-(ethyleneglycol-mono-n-octyl ether) phosphate
di-n-heptenyl phosphate
di-n-octenyl phosphate
di-n-nonenyl phosphate
di-(triethyleneglycol-mono-n-octenyl ether) phosphate
di-(ethyleneglycol-mono-n-heptyl ether) phosphate
di-(7-methyloctyl) phosphate
di-(5-methylhexyl) phosphate
di-(6,6-dimethylheptyl) phosphate
n-hexyl-n-nonyl phosphate, and
n-hexyl-n-octyl phosphate.

The preferred dialkyl phosphate moiety is di-n-octyl phosphate, and the preferred counterion is chosen from sodium, potassium and triethanolammonium.

The amount of dialkyl or dialkenyl phosphate salt which is present in the composition according to the invention is from 1 to 99.9%, preferably from 2 to 50% by weight of the composition.

Compositions containing less than 1% by weight of the dialkyl or dialkenyl phosphate salt show poor lather characteristics and lack the desired feel properties associated with compositions containing higher levels of this ingredient.

The Cosmetically Acceptable Vehicle

The selection of a suitable vehicle will depend on the required product form of the composition. Typically, the vehicle will be chosen from diluents, dispersants or carriers for the dialkyl or dialkenyl phosphate salt, so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1,3-diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polythylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 0.01 to 99.9%, preferably from 50 to 98% by weight of the composition, and can, in the absence of other cosmetic adjuncts, form the balance of the composition.

Water

The composition according to the invention can also comprise water, which can also act as a vehicle for the dialkyl or dialkenyl phosphate salt and to enable it to be provided at a concentration suitable for convenient topical application to human skin.

The amount of water present in the composition of the invention is accordingly up to 99%, preferably from 5 to 99% by weight of the composition.

Co-surfactant

The composition according to the invention can also optionally comprise a co-surfactant, further to modify the surfactant properties attributable to the dialkyl or dialkenyl phosphate salt.

Examples of co-surfactants include anionic surfactants other than the phosphate salts defined herein, as well as nonionic, amphoteric and zwitterionic surfactants.

Anionic Co-surfactants

Particularly preferred co-surfactants, when employed, are anionic surfactants, examples of which are set out hereinafter.

i. Fatty Acid Soap Co-surfactant

The composition according to the invention can optionally comprise, as a co-surfactant one or more soaps which are water-soluble or water-dispersable alkali metal salts of an organic acid, especially a sodium or a potassium salt, or the corresponding ammonium or substituted ammonium salt. Examples of suitable organic acids are natural or synthetic alkanoic acids having from 10 to 22 carbon atoms, especially the fatty acids of triglyceride oils such as tallow and coconut oil.

For solid products, such as powders, bars or tablets, the preferred soap is a soap of tallow fatty acids, that is fatty acids derived from tallow class fats, for example beef tallow, mutton tallow, lard, palm oil and some vegetable butters. Minor amounts of up to about 30%, preferably 10 to 20%, by weight of sodium soaps of nut oil fatty acids derived from nut oils, for example coconut oil and palm kernel oil, may be admixed with the sodium tallow soaps, to improve their lathering and solubility characteristics if desired. Whereas tallow fatty acids are predominantely $C_{14}$ and $C_{18}$ fatty acids, the nut oil fatty acids are of shorter chain length and are predominantly $C_{10}$–$C_{14}$ fatty acids.

For liquid or gel products, the preferred soaps are predominantely $C_{10-14}$ fatty acids derived from nut oils, or alternatively, from synthetic alkanoic acids.

The soaps can be provided as a preformed ingredient for the composition, or they can be formed in situ during the manufacture of the composition by reaction of suitable fatty acids and an alkali.

The amount of fatty acid soap which can be present in the composition according to the invention is up to 90%, preferably from 2 to 80% by weight of the composition.

ii. Non-soap Anionic Co-surfactants

The composition according to the invention can also optionally comprise one or more non-soap anionic co-surfactants, examples of which include:

The alkali metal salts of organic sulphuric reaction products having an alkyl or acyl radical containing from 8–22 carbon atoms and a sulphonic acid or sulphuric acid ester group. Specific examples of these synthetic anionic surfactants are the sodium, ammonium, potassium or triethanolammonium alkyl sulphates, especially those obtained by sulphating the higher alcohols ($C_8$–$C_{18}$), sodium coconut oil fatty acid monoglyceride sulphates and sulphonates; sodium or potassium salts of sulphuric esters of the reaction product of one mole of a higher fatty alcohol (e.g. tallow or coconut oil alcohols) and 1-12 moles of ethyleneoxide; sodium or potassium salts of alkyl phenol ethylene oxide ether sulphate with 1-10 units of ethylene oxide per molecule and in which the alkyl group contains from 8 to 12 carbon atoms, sodium alkyl glyceryl ether sulphonates, the reaction product of fatty acids having from 10 to 22 carbon atoms esterified with isethionic acid and neutralised with sodium hydroxide; water soluble salts of condensation products of fatty acids with N-methyl taurine, Especially preferred non-soap anionic co-surfactants include:
- alkylaryl sulphonates, such as sodium alkyl benzene sulphonate (e.g. TEEPOL CM44, available from Shell).
- alkyl sulphates, such as sodium lauryl sulphate (e.g. EMPICOL CX, available from Albright & Wilson), and triethanolammonium lauryl sulphate (e.g. EMPICOL TL40/T, available from Albright & Wilson).
- alkylether sulphates, such as sodium lauryl ether sulphate (e.g. EMPICOL ESB70, available from Albright & Wilson).
- alkyl sulphonates, such as sodium alkane (C13-18) sulphonate (e.g. HOSTAPUR SAS 30, available from Hoechst).
- olefin sulphonates, such as sodium olefin sulphonate (C15-18) (e.g. HOSTAPUR OS, available from Hoechst).

Sarcosinates, having the structure (3):

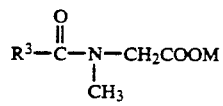

where $R^3$ is chosen from $C_{6-14}$ alkyl, and
M is a counterion chosen from alkali metals, ammonium, substituted ammonium, such as alkanolammonium.

An example of sarcosinates having the structure (3), sodium lauryl sarcosinate (e.g. HAMPOSYL L-95, available from Grace).

Taurides, having the structure (4):

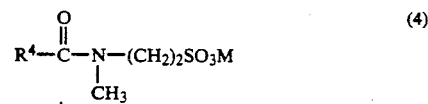

where $R^4$ is chosen from $C_{8-18}$ alkyl
An example of taurides having the structure (4) is:
coconut methyl taurine (e.g. FENOPON TC 42, available from GAF).

Isethionates, having the structure (5):

where $R^5$ is chosen from $C_{8-18}$ alkyl.
An example of isethionates having the structure (5) is:
sodium acyl isethionate (e.g. JORDAPON Cl, available from Jordan).

Monoalkyl sulphosuccinates, having the structure (6):

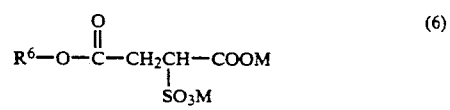

where $R^6$ is chosen from $C_{10-20}$ alkyl.
Examples of monoalkyl sulphosuccinates having this structure (6) include:
- sodium lauryl sulphosuccinate (e.g. EMPICOL SLL, available from Albright & Wilson)
- magnesium alkyl sulphosuccinate (e.g. ELFANOL 616 Mg, available from AKZO),
- sodium lauryl ethoxysulphosuccinate (e.g. EMPICOL SDD, available from Albright & Wilson)
- coconut monoethanolamide ethoxysulphosuccinate, (e.g. EMPICOL SGG)
- disodium lauryl polyglycolether sulphosuccinate (e.g. SURTAGENE S30, available from CHEM-Y)
- polyethyleneglycol sulphosuccinate (e.g. REWOPOL SBFA 30, available from REWO).

Dialkyl sulphosuccinates, having the structure (7):

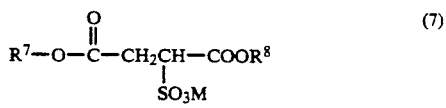

where $R^7$ and $R^8$ are the same or different, and are chosen from $C_{6-14}$ alkyl.

An example of dialkyl sulphosuccinate having the structure (7) is:
sodium dioctyl sulphosuccinate (e.g. EMCOL 4500 available from Witco).

Acyl lactylates, having the structure (8):

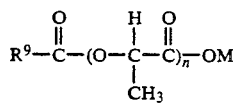

(8)

where $R^9$ is chosen from $C_{6-16}$ alkyl, and n is 1 or 2

An example of acyl lactylates having the structure (8) is: decanoyl lactylate (e.g. PATIONIC 122A, available from Patterson, C. J.).

Acylated α-amino acids, such as sodium lauroyl glutamate (e.g. ACYLGLUTAMATE LS-11, available from Ajinomoto Co. Inc.).

Ethyl carboxylates, such as alkyl $C_{12-14}O(EO)_4OCH_2CO_2Na$ (e.g. AKYPO RLM 38, available from AKZO).

Nonionic Co-surfactants

A composition according to the invention can also comprise nonionic co-surfactants which are compounds produced by the condensation of alkylene oxide groups (hydrophilic in nature) with an organic hydrophobic compound, which may be aliphatic or alkyl aromatic in nature. Examples of nonionic co-surfactants include:

i. The polyethylene oxide condensates of alkyl phenols having from 6 to 12 carbon atoms, either straight or branched chain, with ethylene oxide, which is present in amounts of from 10 to 60 moles of ethylene oxide per mole of alkylphenol.

ii. The condensation product of aliphatic alcohols having from 8 to 18 carbon atoms, straight or branched chain, with ethyleneoxide, for example, a coconut alcohol ethyleneoxide condensate having from 10 to 13 moles of ethylene oxide per mole of coconut alcohol, the coconut alcohol fraction having from 10 to 14 carbon atoms.

iii. Long chain tertiary amineoxides having the structure (9):

(9)

where $R^{10}$ contains an alkyl, alkenyl or monohydroxyalkyl radical of from 8 to 18 carbon atoms, from 0 to 10 ethylene oxide moieties and from 0 to 1 glyceryl moiety, and $R^{11}$ and $R^{12}$ contain from 1 to 3 carbon atoms and up to 1 hydroxy group, for example, methyl, ethyl, propyl, hydroxyethyl, or hydroxypropyl groups.

Especially preferred examples of nonionic cosurfactants include:

alkylethoxylates, such as the DOBANOL series, available from Shell;

esterethoxylates, such as the TAGAT series, available from Goldschmidt;

alkylalkanolamides, such as coconut monoethanolamide (e.g. EMPILAN CME, available from Albright & Wilson), and coconut diethanolomide, (e.g. EMPILAN CDE, available from Albright & Wilson).

sugar esters, such as sucrose laurate and methyl glucose laurate (available from Grillo-Werke A. G.)

esters of glycols, such as ethylene glycol mono stearate.

esters of glycerol, such as glyceryl mono stearate.

ethoxylated sorbitan esters, such as the TWEEN series (available from ICI).

amine oxides, such as alkyldimethyl amine oxide (e.g. EMPIGEN OB, available from Albright & Wilson) and alkylethoxydimethyl amine oxide (e.g. EMPIGEN OY, available from Albright & Wilson).

Zwitterionic and Amphoteric co-surfactants

The composition according to the invention can also contain zwitterionic co-surfactants, which are derivatives of aliphatic quaternary ammonium, phosphonium and sulphonium compounds in which the aliphatic radicals can be straight or branched chain, and where one aliphatic substituent contains from 8 to 18 carbon atoms, and one contains an anionic water-solubilising group, such as carboxyl, sulphonate, sulphate, phosphate or phosphonate.

Examples of zwitterionic co-surfactant include:

4-[N,N-di(2-hydroxyethyl)-N-octadecylammonio]-butane-1-carboxylate, and

5-N,N-di(3-hydroxypropyl)-N-hexadecylammonio]-2-hydroxypentane-1-sulphate.

Particularly preferred zwitterionic co-surfactants are betaines, preferred examples of which are:

Alkyl betaines, having the structure (10):

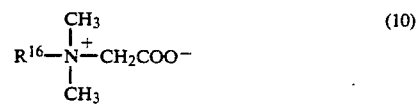

(10)

where $R^{16}$ is $C_{10-16}$ alkyl.

An example of alkyl betaines having the structure (10) is:

lauryldimethyl betaine (e.g. EMPIGEN BB, available from Albright & Wilson).

Alkylamidopropyl betaines, having the structure (11):

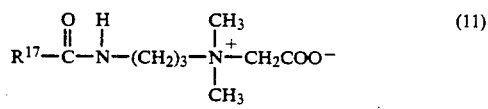

(11)

where $R^{17}$ is $C_{10-16}$ alkyl.

An example of alkylamidopropyl betaines having the structure (11) is:

cocamidopropyl betaine (e.g. TEGOBETAIN L7, available from Goldschmidt).

Alkylamphoglycinates, and having the structure (12):

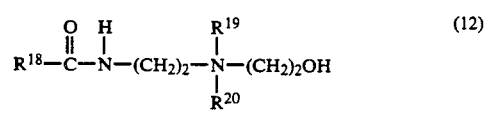

(12)

where $R^{18}$ is $C_{10-16}$ alkyl $R^{19}$ and $R^{20}$ are the same or different and are chosen from H, $CH_2COO^-$ and $(CH_2)_2COO^-$ An example of alkylamphoglycinerates having the structure (12) is:

cocoamphoglycinate (available from GAF), and alkoamphodipropionate.

Sultaines, having the structure (13):

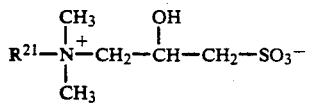

(13)

where $R^{21}$ is chosen from $C_{12-16}$ alkyl or alkylamido.

An example of sultaines having the structure (13) is: cocoamidopropylhydroxysultaine (e.g. CYCLOTERIC BET-CS, available from Alcolac).

Particularly preferred examples of amphoteric co-surfactants include:

Alkoamphoacetates, such as cocoamphoacetate (e.g. MIRANOL CM), and

Alkoamphopropionates, such as cocoamphopropionate (e.g. MIRANOL CM-SF)

both available from Miranol Inc.

The amount of co-surfactant when present in the compositions according to the invention is usually up to 50% preferably from 1 to 40% by weight.

Optional Thickening Agent

The composition according to the invention can also comprise a polymer thickener in an amount sufficient to adjust the viscosity of the composition, so as to facilitate dispensing it conveniently onto the body surface.

Examples of polymer thickeners include:
anionic cellulose materials, such as sodium carboxy methyl cellulose;
anionic polymers such as carboxy vinyl polymers, for examples Carbomer 940 and 941;
nonionic cellulose materials, such a methyl cellulose and hydroxy propyl methyl cellulose;
cationic cellulose materials, such as Polymer JR 400;
cationic gum materials, such as Jaguar C13 S;
other gum materials such as gum acacia, gum tragacanth, locust bean gum, guar gum and carrageenan;
proteins, such as albumin and protein hydrolsates; and
clay materials, such as bentonite, hectorite, magnesium aluminium silicate, sodium magnesium silicate and a synthetic complex clay having the generic formula: $]Si_8Mg_{5.1}Li_{0.6}H_{4.6}O_{24}]^{0.6-}$ $Na+_{0.6}$, an example of which is Laponite, available from Laporte Industries.

The amount of thickening agent which can optionally be employed in the composition according to the invention is normally from 0.05 to 5%, preferably 0.1 to 1% by weight of the composition.

Preservative

The composition according to the invention can also optionally comprise a preservative to prevent microbial spoilage, especially biodegradation of the alkyl phosphate salt. It is accordingly apparent that the composition containing the alkyl phosphate salt may be prone to attack by bacteria, moulds and fungi and other microbial influences. There is therefore a risk that the shelf-life of the composition might be unacceptably short due to the biodegradation or spoilage, unless there is included in the composition a bactericide, fungicide or other microbicide in an amount sufficient to inhibit or prevent the said biodegradation or spoilage, or unless other steps are taken to preserve the composition.

Examples of preservatives include:
(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1,3-diol, phenoxyethanol, dibromodicyanobutane, formalin and Triclosan. The amount of chemical preservative optionally to be incorporated in the composition according to the invention will generally be from 0.05 to 5%, preferably from 0.1 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity $(a_w)$ from 1 to <0.9, preferably to <0.85 and most preferably <0.8, the lowest of these values being that at which yeasts, moulds and fungi will not proliferate.

Further Optional Ingredients

The composition according to the invention can also contain other optional adjuncts, that is ingredients other than the main ingredients already defined which are conventionally employed in compositions for topical application to human skin. Some of these adjuncts, can also function as cosmetically acceptable vehicles and, when present, will normally form the balance of the composition.

Examples of further optional adjuncts include: natural moisturising factors, such as lactic acid, pyrrolidone carboxylic acid or urea; foam controllers; UV absorbers; colourants; and pearlescent agents.

PRODUCT FORM OF THE COMPOSITION

The composition according to the invention can take the form of a liquid or gel, intended to be dispensed from a capped container such as a bottle, roll-on applicator or tube, or a pump-operated or propellant-driven aerosol dispenser, as a skin cleanser, shower product, bath additive or shampoo. The composition can also take for form of a powder or a solid such as a stick, preferably housed in a suitable capped holder with a wind-up or push-up action similar to a lip stick, or a bar or tablet, with or without fatty acid soaps, intended to be used for washing instead of a conventional soap bar.

The invention also provides a closed container containing a detergent composition as herein defined.

Process for Preparing the Composition

The invention also provides a process for preparing the composition of the type defined herein, which process comprises the steps of:

(i) preparing a mixture comprising one or more dialkyl and/or dialkenyl phosphate salts, as defined herein, and one or more cosmetically acceptable vehicles as defined herein, and (ii) subsequently packaging the mixture into containers.

Use of the Composition

The composition according to the invention is intended primarily as a personal washing product for cleansing the face and other sensitive parts of the body surface, including the mucosae. It can also be used for washing the hair as well as the skin.

In use, a small quantity, for example from 1 to 5 ml, of the composition is either rubbed between the hands, together with water to form a foam, which is then used for washing, or applied via a flannel or sponge to the area to be cleansed, or the foam is generated directly on that area. The foam is subsequently rinsed away with clean water.

EVIDENCE TO SHOW ENHANCED LATHER PROPERTIES

Experiments were performed to compare the lather volume obtainable with dioctyl phosphate salt, with that generated using dialkyl phosphate salts outside the scope of the invention, where the alkyl groups contain either less than 7 or more than 9 carbon atoms.

Foam was generated in a standard manner using a Foam Machine whose construction and use will now be described.

The Foam Machine

Foam is generated within a glass graduated cylinder by the action of a perforated piston upon the test composition and a suitably treated substrate. The repetitive compression and expansion of the substrate by the piston results in the aeration of the composition and the generation of foam which accumulates above the piston plate. The volume of the foam can then be read using the graduations of the cylinder when the piston is at its lowest point. The apparatus is enclosed and is supplied with air at a constant temperature of 38° C.

The operation of the machine in detail is as follows. Crimped nylon fibre is soaked in a large quantity of a solution of 2.5% by weight artificial sebum, consisting of squalene, cholesterol, long chain fatty acids, long chain triglycerides and decyl oleate, in dichloromethane for 1 hour. The solvent is poured away, and the fibres are dried by evaporation of residual solvent. The sebum-treated nylon fibre is intended to simulate greasy human skin or hair to which the composition of the invention would normally be applied when washing the skin or shampooing the hair.

Into a graduated glass cylinder of internal diameter 3.8 cm are placed two discs of polyurethane foam (diameter 3.8 cm, height 1.0 cm). 2 g of sebum-treated fibre is placed on top of the foam and the diluted test composition (2 ml) is poured over. The diluted composition is prepared from 7.5 g of test composition and 92.5 g of distilled water.

The prepared cylinder is placed within the foam machine, and with the crosshead at its lowest point the piston plate is adjusted to a level of 70 ml (as determined from the graduations on the cylinder).

The machine is operated with a periodicity of 12 rpm. After each minute of operation, the machine is stopped with the cross-head at the highest point and the volume of foam above the piston plate is recorded.

The machine is operated for a total of 10 minutes, the reported value is the mean of the foam volume values recorded between 3 and 10 minutes inclusive.

Foam Volume Results

All foam values for the dialkyl phosphates were recorded for the triethanolamine salts at pH 8. The percentage surfactant in the composition is based on the weight of the dialkyl phosphate in the acid form, not as the salt.

The following table shows the Foam Volumes obtainable from an aqueous solutions containing $C_{6-10}$ dialkyl phosphates.

| dialkyl phosphate (% w/w) | % w/w | Foam Volume (ml) |
| --- | --- | --- |
| di-n-hexyl phosphate | 20 | 0 |
| di-n-octyl phosphate | 20 | 47.9 |
| di-(2-ethylhexyl) phosphate | 20 | 0 |
| di-n-decyl phosphate | 20 | 12.8 |
| di-n-dodecyl phosphate | 20 | 0 |

From these results, it can be seen that only di-n-octyl phosphate is capable of producing a significant foam. Even the branched chain $C_8$ homologue (i.e. di-(2-ethylhexyl) phosphate produces no measurable foam.

EXAMPLES

The invention is further illustrated by reference to the following examples.

EXAMPLE 1

This Example illustrates a body cleansing liquid product suitable for use in the shower.

The product contains the following ingredients:

| Ingredients | % w/w |
| --- | --- |
| triethanolammonium di-n-octyl phosphate | 36 |
| preservative | 2 |
| water to | 100 |

This product can be used for cleansing the whole body surface, including the hair, for example under the shower, a convenient amount of say 5 ml being placed in the palm of the hand prior to distributing over the body surface with added water to create a lather with superior volume and creaminess characteristics.

Examples 2 to 8 illustrate body shampoos for use in the shower or when bathing.

EXAMPLE 2

| | % w/w |
| --- | --- |
| triethanolammonium di-n-octyl phosphate | 36 |
| triethanolammonium laurate | 1 |
| triethanolammonium myristate | 2 |
| alkyldiaklylamine oxide (EMPIGEN OB: 30% active) | 8.3 |
| myristyldiethylamine oxide | 0.5 |
| cationised cellulose | 0.1 |
| propylene glycol | 10 |
| water to | 100 |

EXAMPLE 3

| | % w/w |
| --- | --- |
| triethanolammonium di-n-octylphosphate | 24 |
| lauryl dimethylbetaine | 3 |
| ethylene glycol monostearate | 1.5 |
| propylene glycol | 2.5 |
| preservative, perfume, dyes | q.v. |
| water to | 100% |

EXAMPLE 4

| | % w/w |
|---|---|
| sodium di-(diethyleneglycol-mono-n-nonyl ether) phosphate | 30 |
| triethanolammonium laurate | 1 |
| triethanolammonium myristate | 2 |
| alkyldialkylamine oxide (EMIGEN OB 30% active) | 8.3 |
| cationised cellulose | 0.1 |
| propylene glycol | 10 |
| water to | 100 |

EXAMPLE 5

| | % w/w |
|---|---|
| triethanolammonium di-(ethyleneglycol-mono-n-octyl ether) phosphate | 20 |
| lauryl dimethylbetaine | 3 |
| ethylene glycol monostearate | 1.5 |
| propylene glycol | 2.5 |
| preservative, perfume, dyes | q.v. |
| water to | 100% |

EXAMPLE 6

| | % w/w |
|---|---|
| triethanolammonium di-(ethyleneglycol-mono-n-heptyl ether) phosphate | 30 |
| triethanolammonium laurate | 1 |
| triethanolammonium myristate | 2 |
| alkyldialkylamine oxide (EMIGEN OB: 30% active) | 8.3 |
| cationised cellulose | 0.1 |
| propylene glycol | 10 |
| water to | 100 |

EXAMPLE 7

| | % w/w |
|---|---|
| sodium di-(7-methyloctyl) phosphate | 25 |
| lauryl dimethylbetaine | 3 |
| ethylene glycol monostearate | 1.5 |
| propylene glycol | 2.5 |
| preservative, perfume, dyes | q.v. |
| water to | 100% |

EXAMPLE 8

| | % w/w |
|---|---|
| sodium di-(di-etyleneglycol-mono-n-nonyl ether) phosphate | 25 |
| cocamidopropyl betaine | 5 |
| preservatives, perfumes, dyes | q.v. |
| water to | 100 |

Examples 9 to 16 illustrate hair shampoos.

EXAMPLE 9

| | % w/w |
|---|---|
| triethanolammonium di-n-heptylphosphate | 20 |
| cocamidopropyl betaine | 1.5 |
| preservatives, dyes, perfumes | q.v. |
| water to | 100% |

EXAMPLE 10

| | % w/w |
|---|---|
| triethanolammonium di-n-nonylphosphate | 10 |
| disodium lauryl sulphosuccinate | 4 |
| cocamidopropyl betaine | 4 |
| preservatives, dyes, perfumes | q.v. |
| water to | 100% |

EXAMPLE 11

| | |
|---|---|
| triethanolammonium di-n-heptenyl phosphate | 20 |
| cocamidopropyl betaine | 1.5 |
| preservatives, dyes, perfumes | q.v. |
| water to | 100% |

EXAMPLE 12

| | |
|---|---|
| triethanolammonium di-n-nonenyl phosphate | 10 |
| disodium lauryl sulphosuccinate | 4 |
| cocamidopropyl betaine | 4 |
| preservatives, dyes, perfumes | q.v. |
| water to | 100% |

EXAMPLE 13

| | % w/w |
|---|---|
| potassium di-(5-methylhexyl) phosphate | 25 |
| cocamidopropyl betaine | 1.5 |
| preservatives, dyes, perfumes | q.v. |
| water to | 100% |

EXAMPLE 14

| | |
|---|---|
| triethanolammonium di-(6,6-dimethylheptyl) phosphate | 10 |
| disodium lauryl sulphosuccinate | 4 |
| cocamidopropyl betaine | 4 |
| preservatives, dyes, perfumes | q.v. |
| water to | 100% |

EXAMPLE 15

| | |
|---|---|
| triethanolammonium di-octenyl phosphate | 15 |
| lauryldimethyl betaine | 6 |
| preservatives, perfumes, dyes | q.v. |
| water to | 100 |

EXAMPLE 16

| | |
|---|---|
| triethanolammonium di-(7-methyloctyl) phosphate | 25 |
| preservatives, perfumes, dyes | q.v. |
| water to | 100 |

Examples 17 to 21 illustrate facial foaming cleansers.

EXAMPLE 17

| | % w/w |
|---|---|
| sodium di-n-octyl phosphate | 30 |
| lauryl dimethyl betaine | 4 |
| sorbitol | 5 |
| glycerol | 2 |
| quaternised cellulosic polymer (Polymer JR400) | 0.3 |
| preservative, dyes, perfumes | q.v. |
| water to | 100 |

EXAMPLE 18

| | % w/w |
|---|---|
| sodium di-(triethyleneglycol-mono-n-octenyl ether) phosphate | 25 |
| lauryl dimethyl betaine | 4 |
| sorbitol | 5 |
| glycerol | 2 |
| quaternised cellulosic polymer (Polymer JR400) | 0.3 |
| preservative, dyes, perfumes | q.v. |
| water to | 100 |

EXAMPLE 19

| | % w/w |
|---|---|
| sodium mono-n-octyl mono-n-hexyl phosphate | 30 |
| lauryl dimethyl betaine | 4 |
| sorbitol | 5 |
| glycerol | 2 |
| quaternised cellulosic polymer (Polymer JR400) | 0.3 |
| preservative, dyes, perfumes | q.v. |
| water to | 100 |

EXAMPLE 20

| | |
|---|---|
| sodium di-n-octylphosphate | 15 |
| sodium di-n-nonylphosphate | 10 |
| sorbitol | 3 |
| preservatives, perfume, dyes | q.v. |
| water to | 100% |

EXAMPLE 21

| | |
|---|---|
| sodium di-(di-ethyleneglycol-mono-n-octyl ether) phosphate | 30 |
| sorbitol | 6 |
| propylene glycol | 2 |
| preservatives, perfumes, dyes | q.v. |
| water to | 100 |

EXAMPLES 22, 23 and 24

The following three examples illustrate soap-containing products with di-n-octyl phosphate salt in accordance with the invention.

In each case, the products were made in accordance with standard soap manufacture. The product of Example 22 yielded a flaked product which could not readily be pressed into a bar, as the flakes were not sufficiently cohesive. With the products of Examples 23 and 24, bars were formed following the usual plodding, extrusion and stamping that is conventional in soap bar manufacture.

These soap products had the following formulations:

| | Examples | | |
|---|---|---|---|
| | 22 | 23 | 24 |
| Ingredient | (% by weight) | | |
| Hardened Tallow Soap | 64 | 66.6 | — |
| 80/20 tallow-coco soap | — | 9 | 76 |
| sodium di-n-octyl phosphate | 16 | 14.4 | 19 |
| water | 20 | 10 | 5 |

We claim:

1. A composition suitable for topical application to the skin or hair, which consisting essentially of:

a. from 1 to 99.9% by weight of a dialkyl or dialkenyl phosphate salt (or mixtures thereof) having the structure (1):

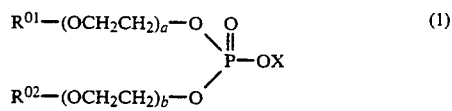

where $R^{01}$ and $R^{02}$ are each chosen from branched or unbranched alkyl or alkenyl groups having an average of from 7 to 9 carbon atoms;

X is chosen from H, alkali metal, ammonium and substituted ammonium counterions;

a and b are each chosen from 0 or a value of from 1 to 4; and b. from 0.01 to 99% by weight of a cosmetically acceptable vehicle for the salt.

2. The composition of claim 1, wherein the dialkyl phosphate moiety of the alkyl phosphate salt is selected from the group consisting of:
di-n-heptyl phosphate
di-n-octyl phosphate
di-n-nonyl phosphate
di-(7-methyloctyl) phosphate
di-(5-methylhexyl) phosphate
di-(6,6-dimethylheptyl) phosphate
di-(ethyleneglycol-mono-n-octyl ether) phosphate
di-(ethyleneglycol-mono-n-heptyl ether) phosphate
di-(diethyleneglycol-mono-n-octyl ether) phosphate
n-hexyl-n-nonyl phosphate, and
n-hexyl-n-octyl phosphate.

3. The composition of claim 1, wherein the dialkenyl phosphate moiety of the alkenyl phosphate salt is selected from the group consisting of:
di-n-heptenyl phosphate
di-n-octenyl phosphate
di-n-nonenyl phosphate, and
di-(triethyleneglycol-mono-n-octenyl ether) phosphate.

4. The composition of claim 1, wherein the dialkyl phosphate salt is a di-n-octyl phosphate salt.

5. The composition of claim 1, wherein the counterion is selected from the group consisting of sodium, potassium or triethanolammonium.

6. The composition of claim 1, wherein the dialkyl or dialkenyl phosphate salt forms from 2 to 50% by weight of the composition.

7. The composition of claim 1, which further comprises an anionic co-surfactant.

8. The composition of claim 1, which further comprises a nonionic co-surfactant.

9. The composition of claim 1, which is a liquid or gel product.

10. The composition of claim 9, which is a washing product suitable for topical application to the face.

11. The composition of claim 1, which is a shampoo.

12. The composition of claim 1, which is a powder.

13. The composition of claim 1, which is a bar or tablet suitable for washing the skin.

14. The composition of claim 13, which is a soap bar or soap tablet.

15. A process for preparing a composition as claimed in claim 1, which process comprises the steps of:
   i. preparing a mixture consisting essentially of:
      a. one or more dialkyl or dialkenyl phosphate salts having the structure (1):

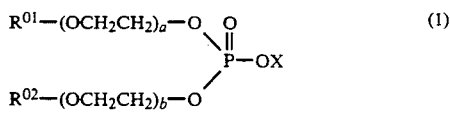

where $R^{01}$ and $R^{02}$ are each is chosen from branched or unbranched alkyl or alkenyl groups having an average of from 7 to 9 carbon atoms;

X is chosen from H, alkali metal, ammonium and substituted ammonium counterions;

a and b are each chosen from 0 or a value of from 1 to 4; and b. a cosmetically acceptable vehicle for the salt, and
   ii. subsequently packaging the composition so formed into containers.

16. A method of cleansing the skin or the hair which comprises the step of applying thereto an effective amount of the composition of claim 1, together with water to form a foam, and subsequently rinsing away the foam with water.

* * * * *